United States Patent
Lachaine et al.

(10) Patent No.: US 9,248,316 B2
(45) Date of Patent: *Feb. 2, 2016

(54) FEATURE TRACKING USING ULTRASOUND

(75) Inventors: Martin Lachaine, Montreal (CA); Sebastien Tremblay, St.-Jean-sur-Richelieu (CA); Fabienne Lathuiliere, Montreal (CA); Tony Falco, La Prairie (CA)

(73) Assignee: ELEKTA LTD., Montreal, Quebec (CA)

(*) Notice: Subject to any disclaimer, the term of this patent is extended or adjusted under 35 U.S.C. 154(b) by 0 days.

This patent is subject to a terminal disclaimer.

(21) Appl. No.: 13/239,795

(22) Filed: Sep. 22, 2011

(65) Prior Publication Data

US 2012/0071758 A1    Mar. 22, 2012

Related U.S. Application Data

(63) Continuation-in-part of application No. 12/956,991, filed on Nov. 30, 2010, now abandoned.

(60) Provisional application No. 61/294,294, filed on Jan. 12, 2010, provisional application No. 61/323,064, filed on Apr. 12, 2010.

(51) Int. Cl.
*A61B 8/00* (2006.01)
*A61N 5/10* (2006.01)
(Continued)

(52) U.S. Cl.
CPC ............ *A61N 5/1049* (2013.01); *A61B 8/085* (2013.01); *A61B 8/4245* (2013.01); *A61B 8/483* (2013.01);
(Continued)

(58) Field of Classification Search
CPC .......... A61B 8/08; A61B 8/483; A61B 8/469; A61B 6/469; A61B 8/085; A61B 8/58; A61B 8/5244; A61B 8/4245; A61B 8/4263; A61B 8/4461; A61B 8/587; A61B 2019/5255; A61B 2019/5263; A61B 2019/5265; A61B 2019/5276; A61B 19/5244; A61N 5/1049; A61N 2005/1058; G06T 2207/10132; G06T 7/204

USPC .................................................. 600/437–458
See application file for complete search history.

(56) References Cited

U.S. PATENT DOCUMENTS

| | | |
|---|---|---|
| 3,082,322 A | 3/1963 | Koerner et al. |
| 3,777,124 A | 12/1973 | Pavkovich |
| 3,987,281 A | 10/1976 | Hodes |
| 3,991,310 A | 11/1976 | Morrison |

(Continued)

FOREIGN PATENT DOCUMENTS

| | | |
|---|---|---|
| CA | 2416887 A1 | 2/2002 |
| CA | 2621741 A1 | 3/2007 |

(Continued)

OTHER PUBLICATIONS

<http://www.gemedicalsystems.com/patient/see_treat/positioning.html>.

(Continued)

*Primary Examiner* — Elmer Chao
(74) *Attorney, Agent, or Firm* — Finnegan, Henderson, Farabow, Garrett & Dunner LLP

(57) ABSTRACT

Various implementations of the invention provide techniques and supporting systems that facilitate real-time or near-real-time ultrasound tracking for the purpose of calculating changes in anatomical features during a medical procedure. More specifically, anatomical features within a patient undergoing a medical procedure are tracked by obtaining temporally-distinct three dimensional ultrasound images that include the feature of interest and obtaining a targeted subset of ultrasound images focused on the feature. Based on the targeted subset of ultrasound images, a displacement of the feature is determined and image parameters used to obtain the targeted subset of ultrasound images are adjusted based on the displacement. This results in a time-based sequence of three dimensional images and targeted ultrasound images of the feature that identify changes in the position, size, location, and/or shape of the feature.

22 Claims, 8 Drawing Sheets

(51) Int. Cl.
  *A61B 8/08* (2006.01)
  *A61B 19/00* (2006.01)
  *G06T 7/20* (2006.01)

(52) U.S. Cl.
  CPC .............. *A61B 8/58* (2013.01); *A61B 19/5244* (2013.01); *G06T 7/204* (2013.01); *A61B 8/4263* (2013.01); *A61B 8/4461* (2013.01); *A61B 8/587* (2013.01); *A61B 2019/5255* (2013.01); *A61B 2019/5263* (2013.01); *A61B 2019/5265* (2013.01); *A61B 2019/5276* (2013.01); *A61N 2005/1058* (2013.01); *G06T 2207/10132* (2013.01)

(56) References Cited

U.S. PATENT DOCUMENTS

| | | |
|---|---|---|
| 4,118,631 A | 10/1978 | Froggatt |
| 4,618,978 A | 10/1986 | Cosman |
| 4,882,741 A | 11/1989 | Brown |
| 4,923,459 A | 5/1990 | Nambu |
| 4,943,990 A | 7/1990 | Schar |
| 5,039,867 A | 8/1991 | Nishihara et al. |
| 5,080,100 A | 1/1992 | Trotel |
| 5,086,401 A | 2/1992 | Glassman et al. |
| 5,099,846 A | 3/1992 | Hardy |
| 5,107,839 A | 4/1992 | Houdek et al. |
| 5,117,829 A | 6/1992 | Miller et al. |
| 5,138,647 A | 8/1992 | Nguyen et al. |
| 5,207,223 A | 5/1993 | Adler |
| 5,222,499 A | 6/1993 | Allen et al. |
| 5,233,990 A | 8/1993 | Barnea |
| 5,291,889 A | 3/1994 | Kenet et al. |
| 5,295,483 A | 3/1994 | Nowacki et al. |
| 5,299,288 A | 3/1994 | Glassman et al. |
| 5,301,674 A | 4/1994 | Erikson et al. |
| 5,379,642 A | 1/1995 | Reckwerdt et al. |
| 5,389,101 A | 2/1995 | Heilbrun et al. |
| 5,391,139 A | 2/1995 | Edmundson |
| 5,397,329 A | 3/1995 | Allen |
| 5,408,101 A | 4/1995 | Wong |
| 5,411,026 A | 5/1995 | Carol |
| 5,438,991 A | 8/1995 | Yu et al. |
| 5,442,675 A | 8/1995 | Swerdloff et al. |
| 5,446,548 A | 8/1995 | Gerig et al. |
| 5,447,154 A | 9/1995 | Cinquin et al. |
| 5,483,961 A | 1/1996 | Kelly et al. |
| 5,511,549 A | 4/1996 | Legg et al. |
| 5,524,627 A | 6/1996 | Passi |
| 5,531,227 A | 7/1996 | Schneider |
| 5,531,520 A | 7/1996 | Grimson et al. |
| 5,553,618 A | 9/1996 | Suzuki et al. |
| 5,591,983 A | 1/1997 | Yao |
| 5,603,318 A | 2/1997 | Heilbrun et al. |
| 5,609,485 A | 3/1997 | Bergman et al. |
| 5,645,066 A | 7/1997 | Gandini et al. |
| 5,673,300 A | 9/1997 | Reckwerdt et al. |
| 5,690,108 A | 11/1997 | Chakeres |
| 5,715,166 A | 2/1998 | Besl et al. |
| 5,734,384 A | 3/1998 | Yanof et al. |
| 5,740,225 A | 4/1998 | Nabatame |
| 5,754,623 A | 5/1998 | Seki |
| 5,757,881 A | 5/1998 | Hughes |
| 5,778,043 A | 7/1998 | Cosman |
| 5,810,007 A | 9/1998 | Holupka et al. |
| 5,836,954 A | 11/1998 | Heilbrun et al. |
| 5,851,183 A | 12/1998 | Bucholz |
| 5,859,891 A | 1/1999 | Hibbard |
| 5,871,445 A | 2/1999 | Bucholz |
| 5,952,577 A | 9/1999 | Passi |
| 5,991,703 A | 11/1999 | Kase |
| 6,019,724 A | 2/2000 | Gronningsaeter et al. |
| 6,038,283 A | 3/2000 | Carol et al. |
| 6,094,508 A | 7/2000 | Acharya et al. |
| 6,106,470 A | 8/2000 | Geiser et al. |
| 6,112,341 A | 9/2000 | Moreland |
| 6,117,081 A | 9/2000 | Jago et al. |
| 6,118,848 A | 9/2000 | Reiffel |
| 6,119,033 A | 9/2000 | Spigelman et al. |
| 6,122,341 A | 9/2000 | Butler et al. |
| 6,129,670 A | 10/2000 | Burdette et al. |
| 6,138,495 A | 10/2000 | Paltieli et al. |
| 6,144,875 A | 11/2000 | Schweikard et al. |
| 6,146,390 A | 11/2000 | Heilbrun et al. |
| 6,198,957 B1 | 3/2001 | Green |
| 6,208,883 B1 | 3/2001 | Holupka et al. |
| 6,259,943 B1 | 7/2001 | Cosman et al. |
| 6,269,143 B1 | 7/2001 | Tachibana |
| 6,276,211 B1 | 8/2001 | Smith |
| 6,285,805 B1 | 9/2001 | Gueziec |
| 6,292,578 B1 | 9/2001 | Kalvin |
| 6,307,914 B1 | 10/2001 | Kunieda et al. |
| 6,314,310 B1 | 11/2001 | Ben-Haim et al. |
| 6,325,758 B1 | 12/2001 | Carol et al. |
| 6,345,114 B1 | 2/2002 | Mackie et al. |
| 6,359,959 B1 | 3/2002 | Butler et al. |
| 6,366,798 B2 | 4/2002 | Green |
| 6,385,286 B1 | 5/2002 | Fitchard et al. |
| 6,385,288 B1 | 5/2002 | Kanematsu |
| 6,390,982 B1 | 5/2002 | Bova et al. |
| 6,405,072 B1 | 6/2002 | Cosman |
| 6,423,009 B1 | 7/2002 | Downey et al. |
| 6,438,202 B1 | 8/2002 | Olivera et al. |
| 6,459,769 B1 | 10/2002 | Cosman |
| 6,491,702 B2 | 12/2002 | Heilbrun et al. |
| 6,511,430 B1 | 1/2003 | Sherar et al. |
| 6,516,046 B1 | 2/2003 | Frohlich et al. |
| 6,535,574 B1 | 3/2003 | Collins et al. |
| 6,546,073 B1 | 4/2003 | Lee |
| 6,553,152 B1 | 4/2003 | Miller et al. |
| 6,560,311 B1 | 5/2003 | Shepard et al. |
| 6,567,684 B1 | 5/2003 | Chenevert et al. |
| 6,585,651 B2 | 7/2003 | Nolte et al. |
| 6,591,127 B1 | 7/2003 | McKinnon |
| 6,600,810 B1 | 7/2003 | Hughes |
| 6,621,889 B1 | 9/2003 | Mostafavi |
| 6,628,983 B1 | 9/2003 | Gagnon |
| 6,631,284 B2 | 10/2003 | Nutt et al. |
| 6,636,622 B2 | 10/2003 | Mackie et al. |
| 6,641,539 B2 | 11/2003 | Hirooka et al. |
| 6,661,870 B2 | 12/2003 | Kapatoes et al. |
| 6,662,036 B2 | 12/2003 | Cosman |
| 6,669,635 B2 | 12/2003 | Kessman et al. |
| 6,683,985 B1 | 1/2004 | Kase et al. |
| 6,690,965 B1 | 2/2004 | Riaziat et al. |
| 6,714,627 B1 | 3/2004 | Brown et al. |
| 6,725,079 B2 | 4/2004 | Zuk et al. |
| 6,728,424 B1 | 4/2004 | Zhu et al. |
| 6,731,970 B2 | 5/2004 | Schlossbauer et al. |
| 6,750,873 B1 | 6/2004 | Bernardini et al. |
| 6,754,374 B1 | 6/2004 | Miller et al. |
| 6,785,409 B1 | 8/2004 | Suri |
| 6,804,548 B2 | 10/2004 | Takahashi et al. |
| 6,842,502 B2 | 1/2005 | Jaffray et al. |
| 6,914,959 B2 | 7/2005 | Bailey et al. |
| 6,915,008 B2 | 7/2005 | Barman et al. |
| 6,968,224 B2 | 11/2005 | Kessman et al. |
| 6,980,679 B2 | 12/2005 | Jeung et al. |
| 7,092,109 B2 | 8/2006 | Satoh et al. |
| 7,095,823 B2 | 8/2006 | Topolnjak et al. |
| 7,260,426 B2 | 8/2007 | Schweikard et al. |
| 7,333,644 B2 | 2/2008 | Jerebko et al. |
| 7,343,030 B2 | 3/2008 | Sawyer |
| 7,430,321 B2 | 9/2008 | Okada et al. |
| 7,438,685 B2 | 10/2008 | Burdette et al. |
| 7,535,411 B2 | 5/2009 | Falco |
| 7,613,501 B2 | 11/2009 | Scherch |
| 7,634,304 B2 | 12/2009 | Falco et al. |
| 7,662,097 B2 | 2/2010 | Falco et al. |
| 7,672,705 B2 | 3/2010 | Lachaine et al. |
| 7,729,744 B2 | 6/2010 | Falco et al. |
| 7,801,349 B2 | 9/2010 | Wang et al. |
| 8,042,209 B2 | 10/2011 | D'Souza et al. |
| 8,232,535 B2 | 7/2012 | Olivera et al. |

(56) References Cited

U.S. PATENT DOCUMENTS

| | | |
|---|---|---|
| 2001/0035871 A1 | 11/2001 | Bieger et al. |
| 2001/0049475 A1 | 12/2001 | Bucholz et al. |
| 2002/0018588 A1 | 2/2002 | Kusch |
| 2002/0065461 A1 | 5/2002 | Cosman |
| 2002/0082494 A1 | 6/2002 | Balloni et al. |
| 2002/0087101 A1 | 7/2002 | Barrick et al. |
| 2002/0122530 A1 | 9/2002 | Erbel et al. |
| 2002/0156375 A1 | 10/2002 | Kessman et al. |
| 2002/0176541 A1 | 11/2002 | Schubert et al. |
| 2002/0183610 A1 | 12/2002 | Foley et al. |
| 2002/0188194 A1 | 12/2002 | Cosman |
| 2003/0018232 A1 | 1/2003 | Elliott et al. |
| 2003/0028401 A1 | 2/2003 | Kaufman et al. |
| 2003/0112922 A1 | 6/2003 | Burdette et al. |
| 2003/0144813 A1 | 7/2003 | Takemoto et al. |
| 2003/0153825 A1 | 8/2003 | Mooradian et al. |
| 2003/0182072 A1 | 9/2003 | Satoh et al. |
| 2003/0231790 A1 | 12/2003 | Bottema |
| 2004/0015075 A1 | 1/2004 | Kimchy et al. |
| 2004/0015176 A1 | 1/2004 | Cosman |
| 2004/0034301 A1 | 2/2004 | Falco |
| 2004/0092815 A1 | 5/2004 | Schweikard et al. |
| 2004/0146137 A1 | 7/2004 | Bruder et al. |
| 2004/0176925 A1 | 9/2004 | Satoh et al. |
| 2004/0184646 A1 | 9/2004 | Oosawa |
| 2004/0252870 A1 | 12/2004 | Reeves et al. |
| 2004/0260142 A1 | 12/2004 | Lovoi |
| 2005/0020917 A1 | 1/2005 | Scherch |
| 2005/0180544 A1 | 8/2005 | Sauer et al. |
| 2005/0251029 A1 | 11/2005 | Khamene et al. |
| 2006/0020195 A1 | 1/2006 | Falco et al. |
| 2006/0074292 A1 | 4/2006 | Thomson et al. |
| 2006/0093205 A1 | 5/2006 | Bryll et al. |
| 2006/0120608 A1 | 6/2006 | Luo et al. |
| 2006/0241443 A1 | 10/2006 | Whitmore et al. |
| 2006/0285641 A1 | 12/2006 | Scherch |
| 2006/0293583 A1 | 12/2006 | Saracen et al. |
| 2007/0015991 A1 | 1/2007 | Fu et al. |
| 2007/0038058 A1 | 2/2007 | West et al. |
| 2007/0055090 A1 | 3/2007 | Neustadter et al. |
| 2008/0039713 A1 | 2/2008 | Thomson et al. |
| 2008/0064953 A1 | 3/2008 | Falco et al. |
| 2008/0219405 A1 | 9/2008 | Falco et al. |
| 2008/0292194 A1 | 11/2008 | Schmidt et al. |
| 2009/0003523 A1 | 1/2009 | Raanes et al. |
| 2009/0093716 A1 | 4/2009 | Deischinger et al. |
| 2009/0110145 A1 | 4/2009 | Lu et al. |
| 2009/0226069 A1 | 9/2009 | Razzaque et al. |
| 2011/0069815 A1 | 3/2011 | Nord et al. |

FOREIGN PATENT DOCUMENTS

| | | |
|---|---|---|
| DE | 10 2008 030 244 A1 | 12/2009 |
| EP | 0647457 A1 | 4/1995 |
| EP | 951697 A1 | 10/1999 |
| EP | 1304960 A1 | 5/2003 |
| EP | 1426806 A2 | 6/2004 |
| EP | 1757228 A1 | 2/2007 |
| FR | 2778574T A1 | 11/1999 |
| JP | 2006000220 A | 1/2006 |
| WO | WO-9902074 A1 | 1/1999 |
| WO | WO-99/06644 | 2/1999 |
| WO | WO-99/26534 | 6/1999 |
| WO | WO-99/27839 | 6/1999 |
| WO | WO-0105316 A1 | 1/2001 |
| WO | WO-0209588 A1 | 2/2002 |
| WO | WO-2006051523 A2 | 5/2006 |
| WO | WO 2009/053896 A2 | 4/2009 |

OTHER PUBLICATIONS

Aoki, Y. et al. *An Integrated Radiotherapy Treatment System and its Clinical Application*, Radiation Medicine, vol. 5, No. 4, pp. 131-141, 1987.

Barratt, Dean C., "Accuracy of an Electromagnetic Three-Dimensional Ultrasound System for Carotid Artery Imaging" from Ultrasound in Medicine and Biology, vol. 27, No. 10, 2001, pp. 1421-1425.

Besl et al., A Method for Registration of 3d Shapes, IEEE Transactions on Pattern Analysis and Machine Intelligence 14(2):239-256 (1992).

Bijhold, J. et al. Fast evaluation of patient set-up during radiotherapy by aligning features in portal and simulator images, Phys. Med. Biol., 1999, vol. 36, No. 12, pp. 1665-1679.

Bijhold, J. *Three-dimensional verification of patient placement during radiotherapy using portal images*, Med. Phys. 20 (2), Pt. 1, Mar./Apr. 1993. pp. 347-356.

Boctor, et al., A Rapid Calibration Method for Registration and 3D Tracking of Ultrasound Images Using Spatial Localizer, Proceedings of the SPIE (2003).

Booth, Modelling, the impact of treatment uncertainties in radiotherapy, University of Adelaide, Mar. 2002), Section 2.4 (http://thesis.library.adelaide.edu.au/uploads/approved/adt-SUA20020816.175301/public/03 chapter2.pdf.

Boyer, A. A review of electronic portal imaging devices (EPIDs), Med. Phys. 19 (1), Jan./Feb. 1992 pp. 1-.

Brigger, et al., "B-Spline Snakes: A Flexible Tool for Parametric Contour Detection," IEEE Transactions on Image Processing, vol. 9, No. 9, Sep. 2000, pp. 1484-1496.

Brujic et al., Analysis of Free-Form Surface Registration, International Conference on Image Processing, pp. 393-396 (1996).

Brunie L. et al. Pre-and intra-irradiation multimodal image registration: principles and first experiments, Radiotherapy and Oncology 29 (1993) pp. 244-252.

Christensen G. E., Inverse consistent registration with object boundary constraints, Biomedical Imaging: Macro to NANO, 2004, IEEE International Symposium on Arlington, VA, USA Apr. 15-18, 2004, Piscataway, NJ, USA, IEEE (4 pages).

Claim Chart for Claim 10 of U.S. Pat. No. 5,447,154.

Cuadra, M.B. et al., Atlas-based Segmentation of pathological MR brain images using a model of lesion growth; Medical Imaging IEEE Transactions on, vol. 23, No. 10, pp. 1301-1314, Oct. 2004.

Cuisenaire, O., <http://www.tele.uci.ac.be/PEOPLE/OC/these/node12.html,> Posted Oct. 5, 1999, Downloaded from the Internet on Aug. 10, 2004.

Cuisenaire, O., <http://www.tele.ucl.ac.be/PEOPLE/OC/these/node75.html,> Posted Oct. 5, 1999, Downloaded from the Internet on Aug. 10, 2004.

Cuisenaire, O., http)/www.tele.ucl.ac.be/PEOPLE/OC/these/node74.html, <http://www.tele.ucl.ac.be/PEOPLE/OC/these/node74.html,> Posted Oct. 5, 1999, Downloaded from the Internet on Aug. 10, 2004.

Czarnota G.J. et al. *Ultrasound imaging of apoptosis: high-resolution non-invasive monitoring of programmed cell death in vitro, in situ and in vivo*, British Journal of Cancer (1999) 81(3), pp. 520-527.

Dubois et al. Intraobserver and Interobserver Variability of MR Imaging- and CT-derived Prostate Volumes after Transperineal Interstitial Permanent Prostate Brachytherapy, Radiology. 207(3):785-9 (1998).

Eggert et al., Simultaneous Registration of Multiple Range Views for Reverse Engineering, International Conference of Pattern Recognition, pp. 243-247 (1996).

European Search Report for PCT/CA2007/001626 dated Nov. 5, 2010 (6 pages).

Hanks, et al. , Three Dimensional Conformal External Beam Treatment of Prostate Cancer http://prostate-help.org/download/pilgrim/10rad.pdf.

Hanks, et al.,Clinical and Biochemical Evidence of Control of Prostate Cancer at 5 Years After External Beam Radiation, The Journal of Urology, vol. 154, 456-459 (1995).

Haralick et al., Pose Estimation From Corresponding Data Point, IEEE Transactions on Systems, Man, and Cybernetics, 19(6):1426-1446 (1989).

Holupka, et al., (1996), "Ultrasound Image Fusion for External Beam Radiotherapy for Prostate Cancer," *J. Radiation Oncology Biol. Phys.*, vol. 35, No. 5, pp. 975-984.

http://www.acmp.org/meetings/hershey_2001/highlights/benedict.pdf.

(56) References Cited

OTHER PUBLICATIONS http://www.emoryradiationoncology.org/high-technology.htm.
http://www.ucsf.edu/ipouliot/Course/chapter5.htm.
http://www.ucsf.edu/ipouliot/Course/conformal_radiation_therapy.htm.
http://www.ucsf.edu/ipouliot/Course/Lesson22.htm.
http://www.varian.com/pinf/imr000c.html.
Hua et al., Development of a Semi-Automatic Alignment Tool for Accelerated Localization of the Prostate, Int. J. Radiation Oncology Biol. Phys., 55(3):811-823 (2003).
International Preliminary Report on Patentability for International Application No. PCT/CA2005/001106 dated Jan. 23, 2007.
International Preliminary Report on Patentability for PCT/CA2005/001428 dated Oct. 3, 2007 (1 page).
International Search Report and Written Opinion for International Application No. PCT/CA2010/002008 dated May 2, 2012, 7 pages.
International Search Report and Written Opinion for PCT/CA2009/000750, mailed Sep. 18, 2009 (8 pages).
International Search Report and Written Opinion of the International Searching Authority for PCT/CA2010/002008 dated Mar. 14, 2011 (7 pages).
International Search Report for International application No. PCT/CA2007/001626 dated Jan. 3, 2008 (4 pages).
International Search Report for PCT/CA2005/001106 dated Nov. 15, 2005.
International Search Report for PCT/CA2005/001428 dated Nov. 16, 2005.
International Search Report for PCT/CA2005/01105 dated Oct. 27, 2005.
International Search Report for PCT/CA2006/001289 dated Oct. 30, 2006 (3 pages).
International Search Report for PCT/CA2006/001461 dated Nov. 30, 2006 (5 pages).
International Search Report for PCT/CA2007/000898 dated Jul. 12, 2007 (3 pages).
Jiang et al., A New Approach to 3-d Registration of Multimodality Medical Images by Surface Matching, SPIE vol. 1808 Visualization in Biomedical Computing,, pp. 196-213 (1992).
Krempien et al., Daily patient set-up control in radiation therapy by coded light projection, 3 pages.
Le Verre, C. et al. *Intensity-Based Registration of Portal Images for Patient Positioning in Radiotherapy.*
Leszczynski K W et al., "An Image Registration scheme applied to verification of radiation therapy" British Journal of Radiology British Inst. Radiol UK [Online] vol. 71, No. 844, Apr. 1998, ISSN: 0007-1285, retrieved from the Internet: url:http://bjr.birjournals.org/cgi/reprint/71/844/413.pdf. [retrieved on Nov. 10, 2009].
Lizzi, Frederic, et al., "Ultrasonic Spectrum Analysis of Tissue Assays and Therapy Evaluation," International Journal of Imaging Systems and Technology, Wiley and Sons, New York, vol. 8, No. 1, (Jan. 1, 1997), pp. 3-10.
Maurer C R et al., Registration of 3-D Images Using Weighted Geometrical Features, IEEE Transactions on Medical Imaging, IEEE Service Center, Piscataway, NJ, US vol. 15, No. 6, Dec. 1, 1996 (14 pages).
Meertens, H. et al. A method for the measurement of field placement errors in digital portal images, Phys. Med. Biol., 1990, vol. 35, No. 3, pp. 299-323.
Mencarelli, et al., "A Dosimetric Method to derive optimal couch corrections in the presence of anatomical deformations for H & N cancer," abstract, 2011, 2 pages.
Michalski et al., Three-Dimensional Conformal Radiation Therapy (3DCRT) for Prostate Cancer, Radiation Oncology Center, Mallinckrodt Institute of Radiology, Washington University Medical Center, St. Louis, Missouri (1996) http://www.phoenix5 org/Infolink/Michalski/#3.
Nagel, et al., "Online dose-guided setup correction protocol for hypofractionated lung radiotherapy," abstract, 2009, 1 page.

Paskalev et al., Daily Target Localization for Prostate Patients based on 3-D Image Correlation, Phys. Med. Biol., vol. 49, pp. 931-939 (2004).
Pennec et al,. A Framework for Uncertainty and Validation of 3-D Registration Methods Based on Points and Frames, International Journal of Computer Vision 25(3), 203-229 (1997).
Pito, *A Registration Aid*, International Conference on Recent Advanced in 3D Digital Imaging and Modelling, pp. 85-92 (1997).
Pollack et al., Conventional vs. Conformal Radiotherapy for Prostate Cancer: Preliminary Results of Dosimetry and Acute Toxicity, Int. J. Radiation Oncology Biol. Phys., 34(3):555-564.
Reinstein, L. et al. *Radiotherapy Portal Imaging Quality, Report of AAPM Task Group No. 28*, American Association of Physicists in Medicine by the American Institute of Physics, New York, 1988.
Robb, *Three-Dimensional Visualization in Medicine and Biology*. Book Chapter in: Handbook of Medical Imaging: Processing and Analysis, ed. Isaac N. Bankman, Academic Press, San Diego, CA, Chapter 42, pp. 685-71 (2000).
Robinson, *Advances in Multi-Modal Data Analysis: The Analyze Software Environment*, <http://www.ii.metu.edu.tr/~med-ii/makaleler/analyze_sw_enve.pdf>, 5 pages. Downloaded on Aug. 10, 2004.
Search Report for European Patent Application No. 06790638.8, mailed Apr. 23, 2010 (7 pages).
Simpson, R.G. et al. *A 4-MV CT scanner for radiation therapy: The prototype system*. Med. Phys. 9(4), Jul./Aug. 1982, pp. 574-579.
Soffen E.M. et al. Conformal static field radiation therapy treatment of early prostate cancer versus non-conformal techniques: A reduction in acute morbidity. Int J Radiat Oncol Biol Phys, 24: 485-488 (1992).
Supplementary European Search Report dated Oct. 25, 2010 (5 pages).
Supplementary European Search Report dated Oct. 30, 2008 for European Patent Application No. 05788508.9/PCT/CA2005001428.
Supplementary European Search Report for PCT/CA2005001106 dated Nov. 10, 2009, 6 pages.
Supplementary European Search Report, for PCT Application No. PCT/CA2005001135, dated Feb. 27, 2009 (12 pages).
Supplementary Partial European Search Report for EP Application No. 5763463, dated Nov. 30, 2009, 7 pages.
Swindell, W. et al. *Computed tomography with a linear accelerator with radiotheraphy applications*, Med. Phys. 10(4), Jul./Aug. 1983, pp. 416-420.
Thayananthan, A. et al., <http://mi.eng.cam.ac.uk/~bdrs2/papers/thayananthan_cvpr03.pdf>, pp. 1-8. Downloaded from the Internet on Aug. 10, 2004.
Tome et al., Commissioning and Quality Assurance of an Optically Guided Three-dimensional Ultrasound Target Localization System for Radiotherapy, Med. Phys., 29(8):1781-1788 (2002).
Troccaz, J. et al. Conformal external radiotherapy of prostatic carcinoma: requirements and experimental results, Radiotherapy and Oncology 29 (1993) pp. 176-183.
Troccaz., J et al. Patient Setup Optimization for External Conformal Radiotherapy, Journal of Image Guided Surgery, 1, pp. 113-120 (1995).
Van de Geijn, J. et al. *A Graticule for Evaluation of Megavolt X Ray Port Films*, Radiation Oncology Biology Physics, Nov. 1982, vol. 8, No. 11 pp. 1999-2000.
Written Opinion for PCT/CA2005/001106 dated Nov. 15, 2005.
Written Opinion of the International Search report for PCT/CA2005/001105 dated Oct. 27, 2005.
Written Opinion of the International Searching Authority for PCT/CA2005/001428 dated Nov. 8, 2005 (6 pages).
Written Opinion of the International Searching Authority for PCT/CA2006/001289 dated Oct. 30, 2006 (6 pages).
Written Opinion of the International Searching Authority for PCT/CA2006/001461 dated Dec. 8, 2006 (5 pages).
Written Opinion of the International Searching Authority for PCT/CA2007/000898 dated Jul. 23, 2007 (6 pages).
Written Opinion of the International Searching Authority for PCT/CA2007/001626 dated Dec. 21, 2007 (7 pages).

(56) References Cited

OTHER PUBLICATIONS

Zhang, Iterative Point Matching for Registration of Free-Form Curves and Surfaces, International Journal of Computer Vision, 13(2):119-152 (1994).

Zitova, B. et al., Image Registration Methods: A survey, Image and Vision Computing, Elsevier, Guildford, GB, vol. 21, No. 11, Oct. 1, 2003 (24 pages).

Preliminary Report for PCT/CA10/002008, mailed Jul. 26, 2012, (5 pages).

Search Report for European Application No. 08783253.1 mailed Dec. 30, 2011 (7 pages).

Sawada et al., A Technique for Noninvasive Respiratory Gated Radiation Treatment System Based on a Real Time 3D Ultrasound Image Correlation: A Phantom Study[a], Med. Phys. 31 (2), Feb. 2004, pp. 245-250.

Supplemental European Search Report issued in European Patent Application No. 10842792.3, dated Feb. 25, 2015.

FEATURE TRACKING USING ULTRASOUND

CROSS-REFERENCES TO RELATED APPLICATIONS

This application is a continuation-in-part of U.S. patent application Ser. No. 12/956,991, filed on Nov. 30, 2010, which claims priority to and the benefit of U.S. provisional patent application Ser. No. 61/294,294, filed Jan. 12, 2010, and U.S. provisional patent application Ser. No. 61/323,064, filed Apr. 12, 2010, each entitled "Feature Tracking Using Ultrasound."

TECHNICAL FIELD

This invention relates to methods for tracking features during a medical procedure.

BACKGROUND INFORMATION

One purpose of radiotherapy is to target a specified anatomical region suspected of having either gross or suspected microscopic disease (sometimes referred to as the clinical treatment volume, or "CTV") with radiation while sparing surrounding healthy tissues and at-risk organs. Typically, a physician outlines the CTV on one or more planning images, such as a computed tomography (CT) image, magnetic resonance (MRI) image, three-dimensional ultrasound (3DUS) image, or a positron emission tomography (PET) scan. A treatment plan is then developed which optimizes the radiation dose distribution on the planning images to best accomplish the prescribed goals. The plan may be based on certain treatment parameters such as beam directions, beam apertures, dose levels, energy and/or type of radiation. The treatment is generally given in a finite number of fractions, typically delivered once a day. During treatment, the patient is positioned relative to the radiation beam prior to each fraction according to the treatment plan.

In practice, a margin is included around the CTV to account for anatomical changes in the CTV and surrounding areas. These changes can result from either interfractional motion, i.e., anatomical differences that develop immediately prior to the current fraction (often due to an inaccurate set-up or actual organ motion such as a different state of bladder fill), or from intrafractional motion, i.e., anatomical motion which occurs during the actual treatment delivery. In some instances, both types of motion may be present. In some instances, intrafractional motion may be cyclical, as caused by breathing, or random, as caused by gas or a steadily increasing bladder volume.

Some conventional image-guided radiotherapy (IGRT) applications may be used to track interfractional motion. Various imaging modalities may be used to implement IGRT, including three-dimensional ultrasound (3DUS) and x-ray imaging of fiducial "seeds" implanted in a patient's organ. Image capture is typically performed once prior to the radiation delivery, and the treatment couch is then adjusted to compensate for any changes in anatomy relative to the treatment plan. The use of IGRT to account for intrafractional motion, on the other hand, is in its infancy and requires continuous imaging throughout the treatment. As trends in radiotherapy begin to move towards fewer fractions and longer treatment times, correcting for intrafractional motion is growing in importance.

One method of tracking intrafractional motion uses x-rays to image fiducials at discrete points in time throughout treatment. However, continuous monitoring is not achievable with this methodology because the x-ray imaging exposure is unbearably high, with an image frequency of once per 30 seconds being the currently acceptable limit. Such procedures still require undesirable extra radiation as well as an invasive fiducial implantation procedure. Further, various surface monitoring technologies have been developed for cyclical intrafractional motion, but these do not provide internal information and are not sufficient in many applications, particularly when random motion occurs. Yet another technology uses beacons which are implanted in the feature of interest, and tracked in real-time using electromagnetic methods. As with fiducials, this procedure also requires an invasive implantation procedure.

Two-dimensional ultrasound (2DUS) can conceivably be proposed for intrafractional motion detection as it is real-time in nature, does not add radiation exposure to the patient during the monitoring process, and does not require implantation of fiducials. Temporally-spaced 2DUS images, as well as three-dimensional ultrasound (3DUS) images, have been proposed to track intrafractional motion during radiotherapy. See, for example, Xu et al, Med. Phys. 33 (2006), Hsu et al, Med. Phys. 32 (2005), Whitmore et al, US 2006/0241143 A1, Fu et al, US 2007/0015991 A1, and Bova et al, U.S. Pat. No. 6,390,982 B1. Some of these disclosures discuss the use of 3DUS probes to obtain a "four-dimensional" image series, however, there remain many obstacles in obtaining and using these images which are not addressed in the current literature.

One conventional three-dimensional (3D) probe utilizes a motorized two-dimensional (2D) probe placed inside a housing that sweeps mechanically within the housing, thus collecting a series of two-dimensional slices to cover the three-dimensional volume. For example, imaging a 10 cm×10 cm area at a given depth using a resolution of 0.5 mm, each sweep requires 200 slices. At a frame rate of 20 Hz, one sweep takes approximately 10 seconds to complete, which precludes effective "real-time" four-dimensional imaging (three physical dimensions changing over time). Moreover, reconstruction of the entire three-dimensional volume takes at least two seconds which further reduces the theoretical three-dimensional refresh rate to 12 seconds, although multi-thread processing may help. Anatomical feature extraction based on the three-dimensional images is also time consuming and may require an additional five seconds. Aspects of this invention allow for real-time, or near-real-time, feature tracking ultrasound imaging during a medical procedure.

SUMMARY OF THE INVENTION

Various implementations of the invention provide techniques and supporting systems that facilitate real-time or near-real-time ultrasound tracking for the purpose of calculating changes in anatomical features during a medical procedure. While the methods are primarily described in terms of a radiotherapy fraction, other applications are contemplated, such as cryotherapy, brachytherapy, high-intensity focused ultrasound (HIFU), as well as imaging procedures such as computed tomography (CT), four-dimensional CT, planar x-ray, PET, MRI, and SPECT, or any other medical procedure where it is important to monitor anatomical features throughout the treatment.

Although primarily concerned with intrafractional motion tracking, in some cases correction for interfractional motion may also be implemented prior to the tracking process. In some cases, a hybrid technique of acquiring a temporally-spaced combination of three-dimensional ultrasound images and targeted subsets of two-dimensional ultrasound images may be used. The two-dimensional ultrasound images are used to increase the frequency of feature tracking to render the process as close to real-time as possible.

In a first aspect, a computer-implemented method for tracking an anatomical feature or features (e.g., an organ, tumor, tumor bed, gland, critical anatomical structure, or other lesion) within a patient undergoing a medical procedure such as radiotherapy, radiotherapy planning, image-guided surgery, or other treatment includes obtaining a three dimensional image of a region that includes the feature being treated and determining the location of the feature within the region. The three dimensional image is obtained at a first periodicity (e.g., every 30 seconds) as to reduce the processing and storage burdens as compared to higher frequencies. In between each three dimensional image, a series of temporally-displaced targeted subsets of ultrasound images focused on the region are obtained at a greater periodicity (e.g., every 0.1-3 seconds), and each is compared with the three dimensional image to determine if there has been any changes to the feature (e.g., movement, morphing). To reduce processing and memory requirements, the targeted subsets are typically of lower quality, resolution and/or represent a smaller area of the region than that of the three dimensional images, thereby allowing for more frequent imaging and comparisons. In some preferred embodiments the targeted subsets are planes of ultrasound data rather than a full reconstructed 3D volume.

In some cases, a determination is made as to whether the displacement exceeds a displacement threshold (such as an upper limit of spatial displacement of the feature of interest) and if so, an updated three dimensional image of the region of interest is obtained sooner than would be obtained according to the first periodicity. The updated three dimensional image maybe used for subsequent comparisons with the targeted set of ultrasound images. In addition (or alternatively) a determination is made as to whether the displacement exceeds a safety threshold and if so, the medical procedure is halted to allow for one or more adjustments to the patient's orientation with respect to a treatment device. In certain implementations, one or more treatment apparatus (e.g., a treatment couch on which the patient is supported and/or a multi-leaf collimator for administering radiation therapy) may be continuously adjusted while treatment is being delivered to compensate for the displacement. The displacement can be the shift and/or rotation of the target's position, of a nearby critical structure, or a combination thereof. In some cases, if the feature tracking algorithm is uncertain of the location of the anatomy of interest for a certain length of time, the beam can be interrupted until the algorithm is able to relocate it. The uncertainty can in some cases be determined by a quality factor which measures the quality of its output.

In some embodiments, image parameters used in obtaining the targeted subset of ultrasound images are adjusted based on the displacement. The displacement threshold may be an upper limit on spatial displacement of the feature or exceeding some predefined change in size. The comparison may, in some cases, include comparing grey-scale values of subsequent images to determine the displacement or shift of the feature.

The targeted subset may be a series of two dimensional image slices of the feature, a combination of two or more tracking planes (such as two orthogonal planes), which may, in some cases, be reconstructed as a set of voxels intersecting the planes. The images may be used as obtained, or, in some cases segmented. The images may be obtained from various angles and directions aimed at the feature, including, for example transperineally in the case of a prostate gland. In certain implementations, the targeted subset may be three dimensional ultrasound datasets related to a limited region of interest, which may be determined on an adjusted sector size, an adjusted image depth and/or an adjusted ultrasound sector angle and in some cases have a reduced resolution. In some embodiments, the targeted subset may be a series of 2D slices in a non-Cartesian coordinate system, such as a cylindrical coordinate system. In these cases, the slices may be compared to a previously acquired set of slices through a non-Cartesian registration algorithm.

In some cases, the displacement may be calculated at a frequency greater than the acquisition of images throughout the region of interest. In these cases, the displacement may be based on a set of image data which has not been completely updated since the last displacement calculation.

The three dimensional ultrasound images may be obtained using a motorized probe, a bi-planar probe or a matrix probe, any of which may be internal or external to the patient. In some instances, the probe may have traceable markers attached to it and be calibrated to pixels within the images to facilitate spatial tracking over time with respect to a particular coordinate system. In some cases, the probe is fixed relative to a treatment couch, and the relationship of the probe to the room coordinate system is mapped thereto based on knowledge of the position and orientation of the couch.

The feature to be tracked can be the target lesion being treated, a subset of the lesion, another feature which is proximal to the lesion, a fiducial, or any other feature deemed to be of importance during the medical procedure. In some cases multiple features may be tracked simultaneously. Features may be extracted from both full three-dimensional ultrasound images as well as the targeted subset of ultrasound images to obtain a representation of the feature's motion in time, using either segmentation, registration, non-Cartesian registration or pattern recognition algorithms.

In another aspect, a system for tracking an anatomical feature within a patient undergoing a medical procedure includes a processor and a memory register. The processor is configured to locate the feature of interest within a series of three dimensional images and iteratively compare temporally displaced targeted subsets of ultrasound images obtained at a periodicity greater than the first periodicity with the three dimensional image. The processor then determines, based on each comparison, a displacement of the feature of interest. The register receives and stores the images.

In some versions, the processor determines if the displacement exceeds a displacement threshold (an upper limit of spatial displacement of the feature of interest for a certain length of time, for example, or a quality factor below a certain threshold) and if so, provide instructions to obtain an updated three dimensional image of the region of interest sooner than would be obtained based on the first periodicity. The processor may also determine if the displacement exceeds a safety threshold. If so, the processor can provide instructions to halt the medical procedure, thereby allowing for adjustments to be made to the patient's orientation with respect to a treatment device and/or to the orientation of the treatment device itself prior to reinstating the procedure. In some cases, the full three-dimensional image of the region of interest is only obtained when the displacement threshold is surpassed, which may not occur with any regularity.

In some cases, the system also includes an ultrasound probe for providing the images to the register. The probe may be a two dimensional ultrasound probe rotatably mounted into a housing such that the probe can move according to at least one degree of freedom, either longitudinally, in a sweeping motion about an axis or rotating about an axis. A motor may provide movement to the probe, based, for example, on instructions from a controller to alter the position of the probe relative to the patient, the housing or both. The controller may also provide additional adjustments to one or more imaging parameters. Some embodiments may also provide a display and/or input devices, thus allowing an operator to view the images and interact with the system.

Changes identified in the feature may trigger a warning message (either visual, textual, audio or some combination thereof), warning the operator that the medical procedure should be modified or that the feature can no longer be tracked with sufficient certainty. In other implementations, the changes may cause continuous or semi-continuous modifications to the treatment as it progresses.

BRIEF DESCRIPTION OF FIGURES

In the drawings, like reference characters generally refer to the same parts throughout the different views. Also, the drawings are not necessarily to scale, emphasis instead generally being placed upon illustrating the principles of the invention.

DETAILED DESCRIPTION

Throughout the following descriptions and examples, aspects and embodiments of the invention are described in the context of tracking intrafractional motion during the delivery of radiotherapy. However, it is to be understood that the present invention may be applied to tracking attributes of virtually any feature within or on a patient during any form of medical procedure requiring anatomical tracking, such as external beam and brachytherapy, cryotherapy, hyperthermia, high intensity focused ultrasound treatments (HIFU)) and/or various forms of imaging (e.g., CT, 4DCT, PET, US, SPECT, and MRI).

Figure 1:
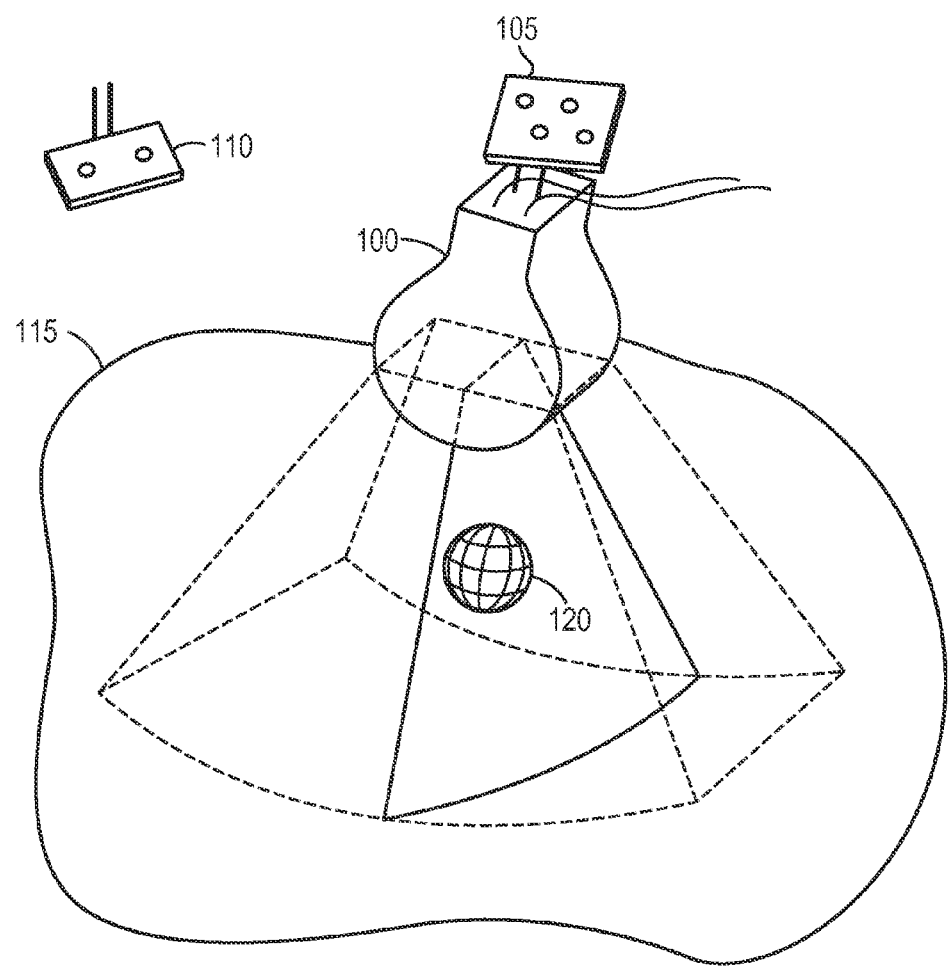
FIG. 1 is a schematic diagram illustrating the use of a mechanical three-dimensional probe, referenced to a room coordinate system, for imaging a feature within a patient according to various embodiments of the invention.

Referring to FIG. 1, a motorized, mechanically sweeping three-dimensional ultrasound probe 100, which is of particular use in this application, contains a two-dimensional probe inside of a housing, the two-dimensional probe being able to sweep at different angles within the housing, controlled by a motor. In certain applications, tracking markers 105 are affixed to the probe handle such that the position of the probe can be detected by a tracking system 110. One such tracking device utilizes an infrared optical camera, which tracks infrared signals emitted from or reflected by the markers. The position and orientation of the probe housing can therefore be determined at all times, based on a relative coordinate system. In certain applications, the individual ultrasound pixels are referenced to a coordinate system useful for the medical procedure, which can for example be tied to room, a treatment device, an imaging device, or a patient.

Because the motorized sweeping probe is essentially a two-dimensional probe that moves according to a particular degree of freedom inside the housing, its position within the housing can be quantified in terms of a parameter X. The parameter X can be measured as an angle in the case of rotational sweep inside the housing, or as a distance in the case of a linear sweep. The parameter X can be controlled by a controller through an interface to the motor. For example, the controller may instruct the motor to move the two-dimensional probe to a particular location within the housing such that a two-dimensional frame can be acquired at a fixed position X. In other cases, the controller may instruct the motor to continuously move probe within the housing, facilitating the acquisition of a three-dimensional sweep by acquiring a series of temporally-displaced image frames while continuously changing X.

In some applications, pixels in a given two-dimensional frame at position X are known relative to a fixed room coordinate system. One method of attributing coordinates to the pixels is to use a calibration algorithm similar to those developed for freehand 3DUS imaging, but using a fixed $X=X_{cal}$, which relates all pixels in a "calibration slice" to the probe markers and hence to the room coordinate system. Known geometry of the three-dimensional probe can then be used to relate this calibration to the slices with other X values.

Calibration may also be achieved by temporarily affixing the three-dimensional probe to a phantom having embedded geometrical features. In such cases, a CT scan of the probe and phantom assembly is acquired, and then a three-dimensional sweep is acquired with the probe still fixed relative to the phantom. The 3DUS images are aligned relative to the CT scan using software that allows rotations and translations of the images such that the geometrical features visible in the 3DUS images match those as seen on CT. In some cases, segmented features extracted from the CT may be used instead of the CT pixel values themselves. The markers affixed to the probe handle are also visible on CT, and thus a relationship between the 3DUS pixels and the markers can be quantified, thus allowing each 3DUS pixel to be known relative to the markers. The pixels can then be referred back to the room coordinate system using known techniques used in the art for freehand 3DUS imaging.

For intrafractional tracking of a structure or anatomical feature, the probe is placed on the patient 115 prior to treatment such that the target 120 is within the field of view of the probe. The technique may be used, for example, for transperineal imaging of the prostate, or imaging of a breast tumor. A full three-dimensional image of the target structure 120 and its surrounding anatomy is acquired by continuously varying X, during which the ultrasound images are acquired at a given frame-rate f The frame-rate is primarily limited by ultrasound physics such as the time needed to send and receive a sound wave, but also may be limited by hardware and computer processing constraints. A typical frame-rate is on the order of 20 Hz. As described above, the pixels in each frame at a known X can be attributed to certain coordinates in the room coordinate system, and therefore the two-dimensional slices can be used to form a "reconstructed" 3DUS volume in reference to the room coordinate system.

Prior to radiotherapy, the patient is typically placed on the treatment table according to skin markings. Correction for interfractional motion can then be performed by imaging of the target or a proximal feature and adjusting the patient's position relative to the room coordinate system either by moving the patient, the couch, or both. This corrects for daily setup errors as well as changes in the anatomy since the treatment planning phase, and can be done with any number of known IGRT techniques. In some cases, this process may be accomplished by acquiring a first three-dimensional sweep of the target structure with the mechanized probe. Typically, the patient couch is moved to correct for initial target misalignments, although other strategies can be used such as modifying the treatment plan. However, this initial interfractional correction does not account for motion during the treatment itself (intrafractional motion), as addressed below.

After initial patient setup, successive temporally-displaced three-dimensional sweeps of the target structure, or more generally of anatomical features related to or near the target structure or other area of interest, can be acquired using the mechanized probe. Displacement of the feature or features in each successive image relative to previous images can then be determined. In one method, a difference in the grayscale between the images is quantified using, for example, a rigid or deformable registration algorithm, or, in other cases, a segmentation algorithm is used to recontour the features in each image and the displacement between successive segmentations is determined. One or more treatment parameters may then be modified as the feature changes location or form. These modifications can be, but are not limited to: warning the operator that the feature has moved outside a given tolerance and instructing her to halt treatment and reposition the patient; automatically halting the treatment beam by synchronizing with the linear accelerator if the feature moves past a given tolerance; correcting for the displacement by automatically adjusting the couch, and then turning on the beam again; iteratively adjusting the beam (for example, by moving the couch, the beam, or both) as the linear accelerator is turned off and on; and/or continuously changing the beam shapes or alignment in synchrony with newly updated feature positions. In some cases, no modification is instituted if the feature has not changed or the changes are within allowable tolerances. In other cases, modifications to the treatment are only effected if the displacement occurs for a predetermined length of time relative to the entire treatment time. For example, if the feature is outside of treatment margins for only a few seconds, this may be permissible during a treatment lasting ten minutes, and therefore no compensation is needed.

In some cases, the registration, segmentation, or other algorithm(s) used to track changes in the feature may have a measurement, such as a quality factor, that indicates the certainty and/or reliability of the image. A threshold can be placed on this quality factor, and if the quality is below this threshold for a predetermined amount of time, the user is warned and/or the treatment halted until the feature can be more reliably tracked.

Although successive acquisition of three-dimensional images may be useful, the images are not truly real-time because of the time delay inherent in the "sweep" process. More specifically, the sweeping technique includes varying X during the sweep to acquire enough frames for reconstruction without gaps between the frames, which is limited by the frame-rate of the ultrasound (which itself is limited by ultrasound physics), creating a full three-dimensional reconstruction of the two-dimensional slices into a full three-dimensional ultrasound volume, and calculation of a representation of the feature from the images.

Strategy 1: Hybrid Three-dimensional and Two-dimensional Temporal Tracking.

Figure 2:
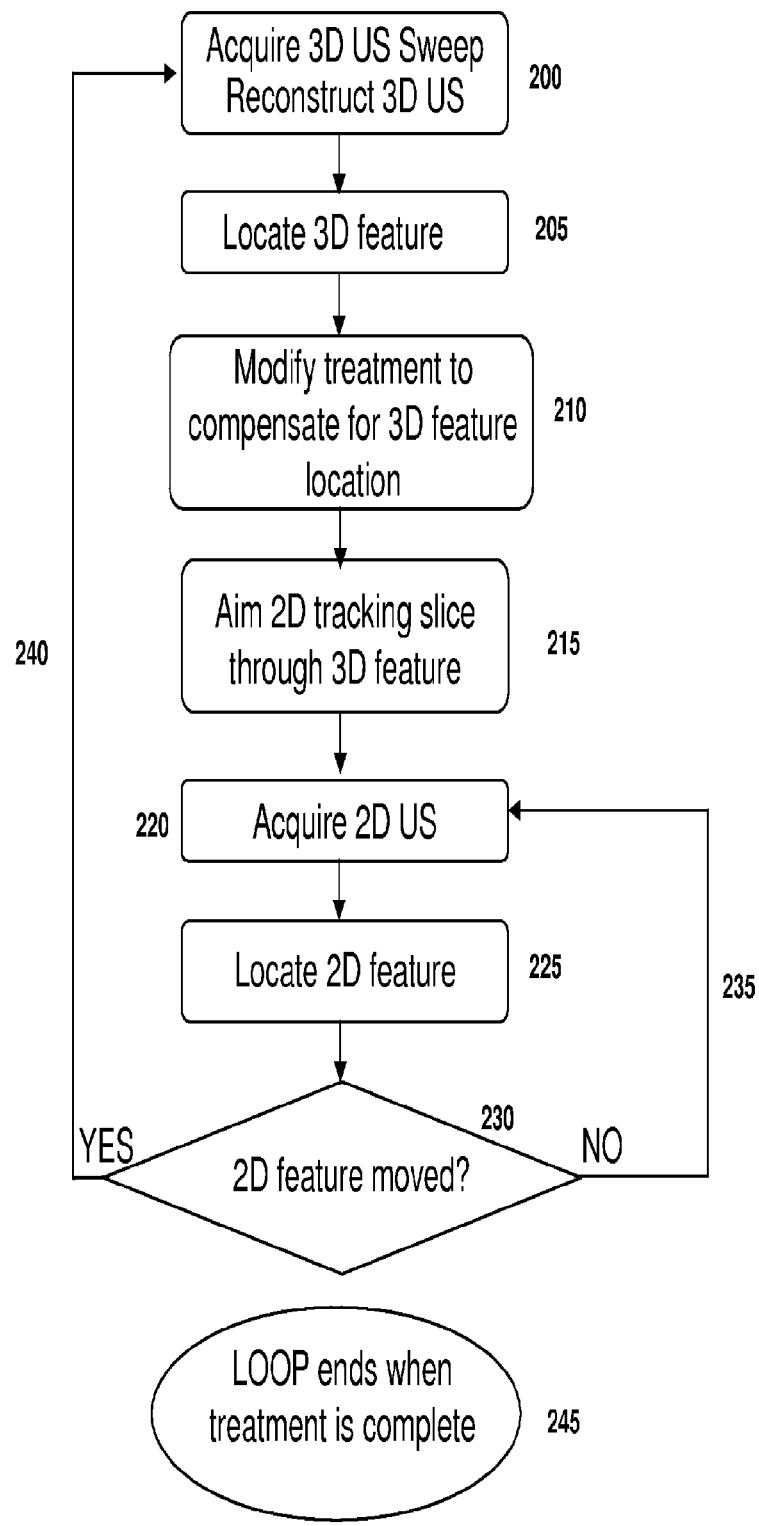
FIG. 2 is a flow-chart illustrating a method for implementing a hybrid three-dimensional and two-dimensional temporal tracking strategy according to various embodiments of the invention.

One approach to using ultrasound for real-time treatment monitoring uses targeted subsets of three-dimensional ultrasound images ("TUS"), and is illustrated in FIG. 2. In step 200, a full three-dimensional sweep of the patient's anatomy, including the feature to be tracked, is acquired by continuously (or in many small discrete steps) varying X to acquire a full set of two-dimensional slices. The two-dimensional slices are then reconstructed in the room coordinate system, using each tagged X-position of the slices as well as the tracking camera information and calibration information, to form a 3DUS image.

In step 205, the three-dimensional feature is located in the 3DUS image. This feature is referred to herein as the three-dimensional feature, as it is determined from a three-dimensional image, as opposed to a feature in a two-dimensional slice image, which is referred to as a two-dimensional feature. The location can be determined manually, semi-automatically, or fully automatically. For example, a three-dimensional pattern recognition algorithm or a three-dimensional rigid registration algorithm or a deformable registration algorithm may be used. In some embodiments, the user can place one or more "hint points" (i.e., one point in the center or 4-8 points on the feature edges), to initiate a segmentation algorithm which then determines the full feature surface in three dimensions. Alternatively, a contour from a planning session can be superimposed onto the three-dimensional image as an initial guess, and potentially warped to better fit the edges in the current image.

In step 210, the treatment is modified to account for the current position of the feature as found in step 205. This can be accomplished, for example, by moving the couch to align the feature (either manually or automatically) if the feature does not significantly change volume or shape. The beam may be temporarily stopped in some cases to allow for the couch motion. Other strategies may include completely recalculating the treatment plan, or re-shaping the beam apertures to better target the feature.

In step 215, the X-position of the motorized probe is moved to a fixed position such that the two-dimensional ultrasound slice is optimally aimed at the feature. For example, if the feature is a segmented organ such as the prostate or a segmented breast lumpectomy cavity, the beam can be aimed at the center of the structure. In another example, the transformation between the slice and a previous reference slice can be calculated using a 2D registration algorithm. The optimal slice location can alternatively be selected based on feature discernibility statistics extracted from the three-dimensional image at step 205. In step 220, a two-dimensional ultrasound slice is acquired at this fixed X-position, which is targeted at the feature, and in step 225 the two-dimensional feature is located in this ultrasound slice. In step 230, if size, shape and/or locational characteristics of the feature have not changed since step 205, another two-dimensional acquisition and feature location is executed (step 235). The process is then repeated until changes in the two-dimensional feature are identified.

A change may include, for example, that the feature has moved outside of the two-dimensional plane, which would result in a significant change in the grayscale values in the region of interest surrounding the feature. The change may also be due to movement of the feature within the two-dimensional plane by an amount greater than a pre-determined threshold, or that the feature has changed shape greater than a predetermined threshold. For prostate imaging, the two-dimensional plane is typically aligned with the sagittal plane which can detect anterior/posterior and superior/inferior motions, which are the most common, with left-to-right motions being much less common. An acceptable threshold may be 2 mm, meaning so long as the prostate center moves by less than 2 mm, step 235 is continued. If the displacement is greater than 2 mm (or some other threshold), the process moves to step 240. Other reasons to transition to step 240 include if the two-dimensional prostate area changes significantly from one frame to the next, which implies that the prostate has moved out-of-plane—either to the right or left, or if the tracking of the feature is lost within a degree of certainty. In some embodiments, step 235 is only initiated if changes are detected for a given amount of time deemed to be non-negligible relative to the total treatment time. In some applications, the location, alignment and/or orientation of the probe may be altered by a robotic arm into which the probe is placed.

At step 240, a new full 3DUS sweep is initiated, and the process is repeated. The entire flowchart loop is continued until the treatment is completed. Using this methodology, three-dimensional acquisition is triggered if motion is detected based on two-dimensional image acquisitions, which, due to the lower processing demands, allows for real-time monitoring. As such, a full three-dimensional adaptation of the treatment is triggered only if it appears that the feature has moved out of tolerance. In some embodiments, step 240 is initiated not only if the feature has likely moved out of tolerance, but also at regular temporal intervals (e.g., every fifteen seconds) as an extra check.

This approach may be used in applications when movement has a high likelihood to be in a particular two-dimensional plane chosen by the orientation of the motorized probe. In some variations, when this likelihood is high, modification of the treatment can be added as a step between 225 and 230 such that the two-dimensional tracking info is used to identify treatment modifications in real-time.

Strategy 2: Hybrid Three-dimensional and Multiple Two-dimensional Plane Temporal Tracking.

Figure 3:
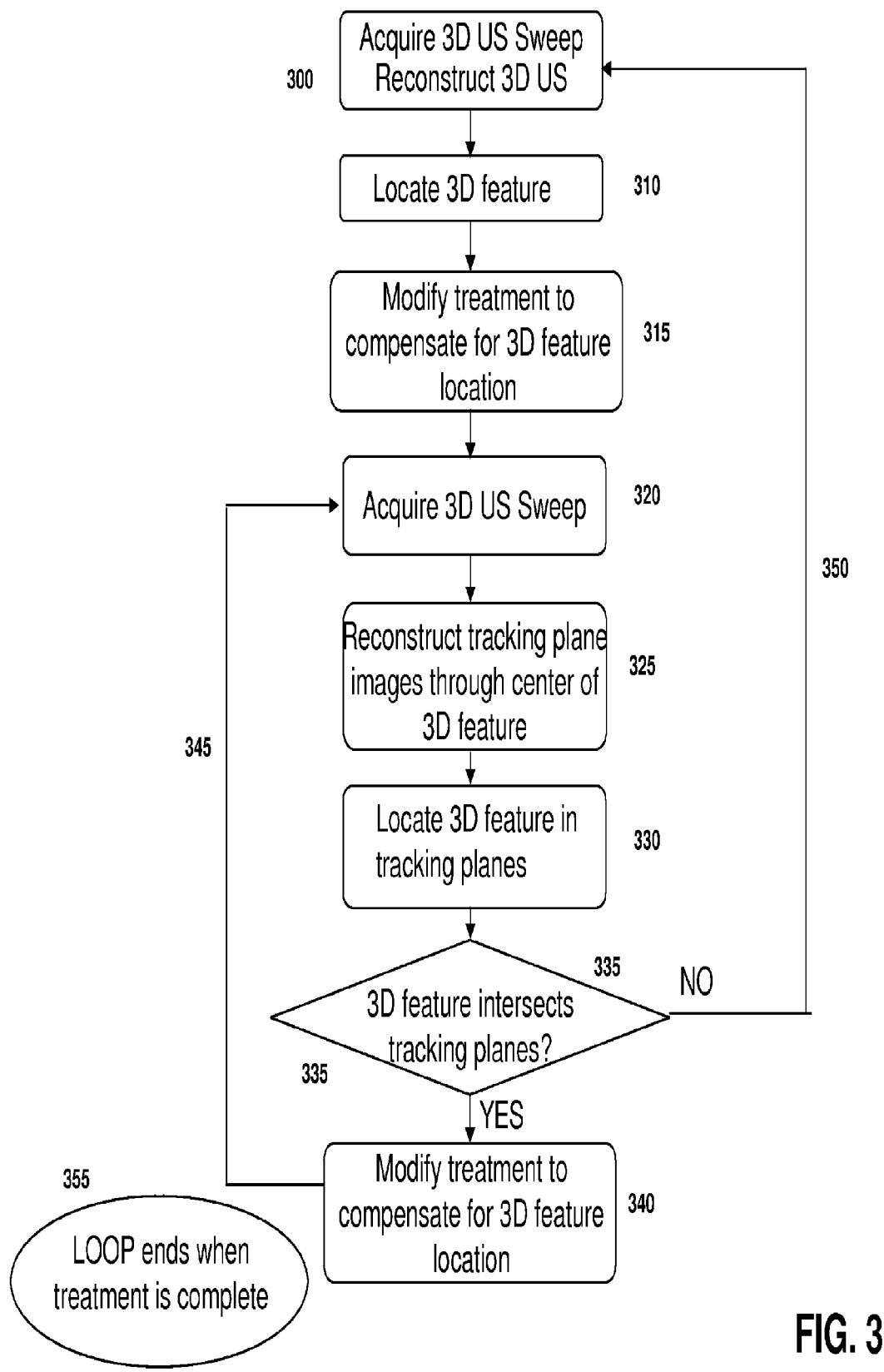
FIG. 3 is a flow-chart illustrating a particular implementation of a hybrid three-dimensional and multiple two-dimensional plane temporal tracking strategy according to various embodiments of the invention.
Figure 4:
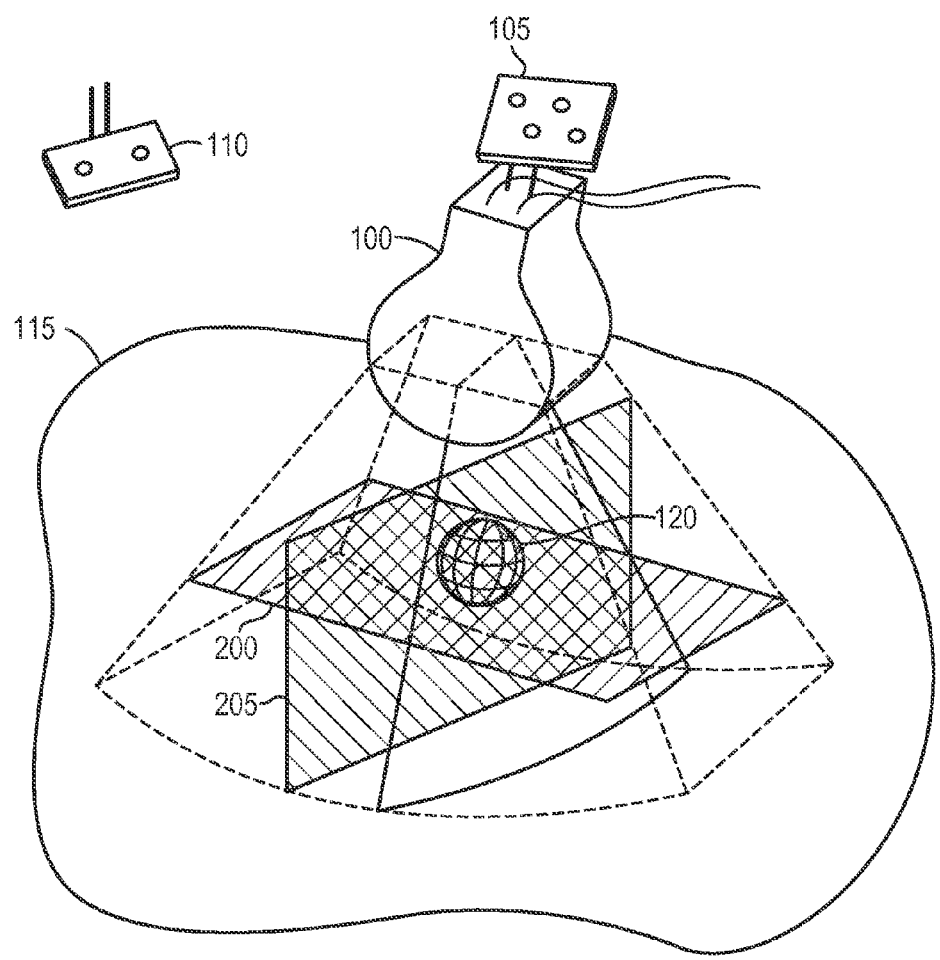
FIG. 4 illustrates the use of tracking planes in the method of FIGS. 2 and 3.

In some applications in which the motion is not likely to be primarily constrained to a particular two-dimensional plane, a hybrid of three-dimensional and multiple two-dimensional plane temporal tracking techniques may be used. Referring to FIG. 3, steps 300, 310 and 315 are the same as 200, 210 and 215 of FIG. 2, respectively. In step 320, a full sweep is acquired by the motorized probe. In step 325, instead of reconstructing the entire three-dimensional image set, only the pixels in two or more tracking planes, preferably being orthogonal or close to orthogonal to each other, are reconstructed. An example is shown in FIG. 4, showing tracking planes 200 and 205 being used for reconstruction.

The planes are selected so as to intersect with the feature 120. In the case of an organ such as the prostate, the planes preferably intersect through the center of the organ, which can be found from computing the centroid of the segmented structure. As used herein, "reconstructed ultrasound plane" refers to a reconstruction of a voxel set attached to a single plane, as opposed to a complete three-dimensional reconstruction that reconstructs the entire 3D voxel set. While limiting the information available to only certain planes, the computational requirements to produce only the reconstructed ultrasound plane(s) are significantly lower. As such, step 325 saves time and memory space, since it is much quicker and more efficient to reconstruct pixels in planes than an entire voxel space, as well as locate changes in features, thus reducing temporal intervals between successive localizations. In some cases, one of the tracking planes is not a reconstructed plane, but consists of the pixels from an actual two-dimensional ultrasound image from a fixed position (at one particular X location) of the motorized probe, as described above in reference to FIG. 2.

Figure 3A:
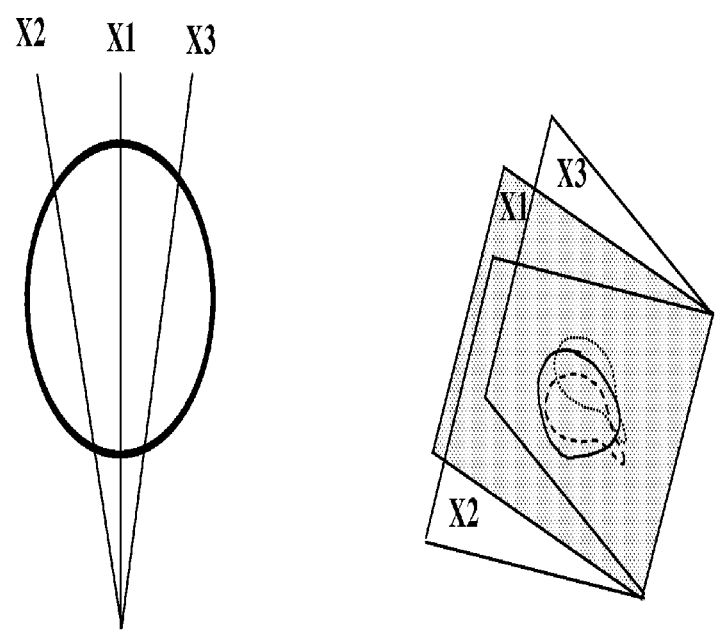
FIG. 3A illustrates a particular implementation of a hybrid three-dimensional and multiple two-dimensional plane temporal tracking technique according to various embodiments of the invention.

In other applications, none of the tracking planes are reconstructed, but consist of pixels from multiple two-dimensional ultrasound images obtained from different positions of the motorized probe along the X plane. For example, as shown in FIG. 3A, three plane positions can be selected, at positions $X_1$ (in the center of the feature), $X_2$ (to the left of center but still imaging part of the feature) and $X_3$, (to the right of center but still imaging part of the feature). The probe can then obtain images at each of these positions in rapid succession and in any convenient order without need for reconstruction. The X positions relative to the center of the feature can be strategically determined based, for example, on knowledge of the three-dimensional surface of the feature. In another example, the multiple plane images are acquired but using a limited range of X values, for example to cover a central portion of the anatomy that is sufficient to determine its position.

Referring back to FIG. 3, in step 330, the three-dimensional feature is located in the tracking planes, creating a three-dimensional surface, that when intersected by a plane, produces a two-dimensional curve. In one method, the shape and volume of the three-dimensional feature, as found in the first iteration of step 310, is assumed to remain constant. By determining where the two-dimensional curves generated by cutting through the tracking planes best fit the grayscale values yields the desired three-dimensional location of the surface, and thus displacement of the feature relative to its position at the previous point in time. "Best fit" can mean, for example, maximization of the sum of image gradients along the curves.

Finding the location of the three-dimensional feature from the tracking planes assumes that at least part of the feature is visible in at least two planes, and increasing the number of planes (e.g., from two to three, or even higher), increases the likelihood that the feature is visible. In some cases, the feature may move to a position where it is no longer visible, as determined at step 335. This determination can be made based on a failure of the process at step 330, for example. If, however, the feature remains visible in one or more of the planes, the treatment is modified to account for the new position (step 340) and acquisition of tracking plane data continues (step 345) to make further adjustments. The position of the tracking planes in 325 may be re-centered to account for the displaced feature found in 330. In the case where feature is no longer in the planes, the full 3DUS volume is reconstructed (step 350). This allows for re-centering of the tracking planes for further iterations, and to ensure that the tracking planes intersect the feature being tracked. The process illustrated in FIG. 3 ends once the treatment is complete (step 355). In some variations, path 350 will be taken even if the feature is still intersected by the tracking planes, at fixed time intervals in order to gather full three-dimensional data at various points in time.

Using this approach, the full three-dimensional displacement can be calculated as long as the tracking planes intersect with the feature, thus reducing the number of times the full three-dimensional image needs to be reconstructed. In contrast to the hybrid three-dimensional and two-dimensional temporal tracking approach, the use of two-dimensional planes allows much faster monitoring of the feature because it does not necessitate full sweeps on the structure, even if a full three-dimensional image is reconstructed any time there is a significant change in the feature.

Strategy 3: Hybrid Three-dimensional and Low-resolution Three-dimensional Temporal Tracking.

In another approach, a series of alternating high (full three-dimensional) and low resolution ("targeted"), ultrasound sweeps are used to track the volume and followed with full volume reconstruction. Reducing the resolution allows for faster sweeps, but due to the limited frame-rate of the ultrasound, fewer two-dimensional slices are acquired for the reconstruction. For example, the high resolution three-dimensional images may be acquired at a periodicity of every thirty seconds, whereas the lower resolution images are obtained every 0.1-3 seconds. A new high-resolution image is captured for every period, unless the comparison between the high-resolution and low-resolution images indicated the violation of a displacement threshold, in which case a new high-resolution image is obtained sooner than would have been taken otherwise. In some cases, the displacement may be sufficient to halt treatment altogether and adjust the patient, the treatment device or both.

Strategy 4: Hybrid Three-dimensional and Limited ROI Three-dimensional Temporal Tracking.

Figure 5:
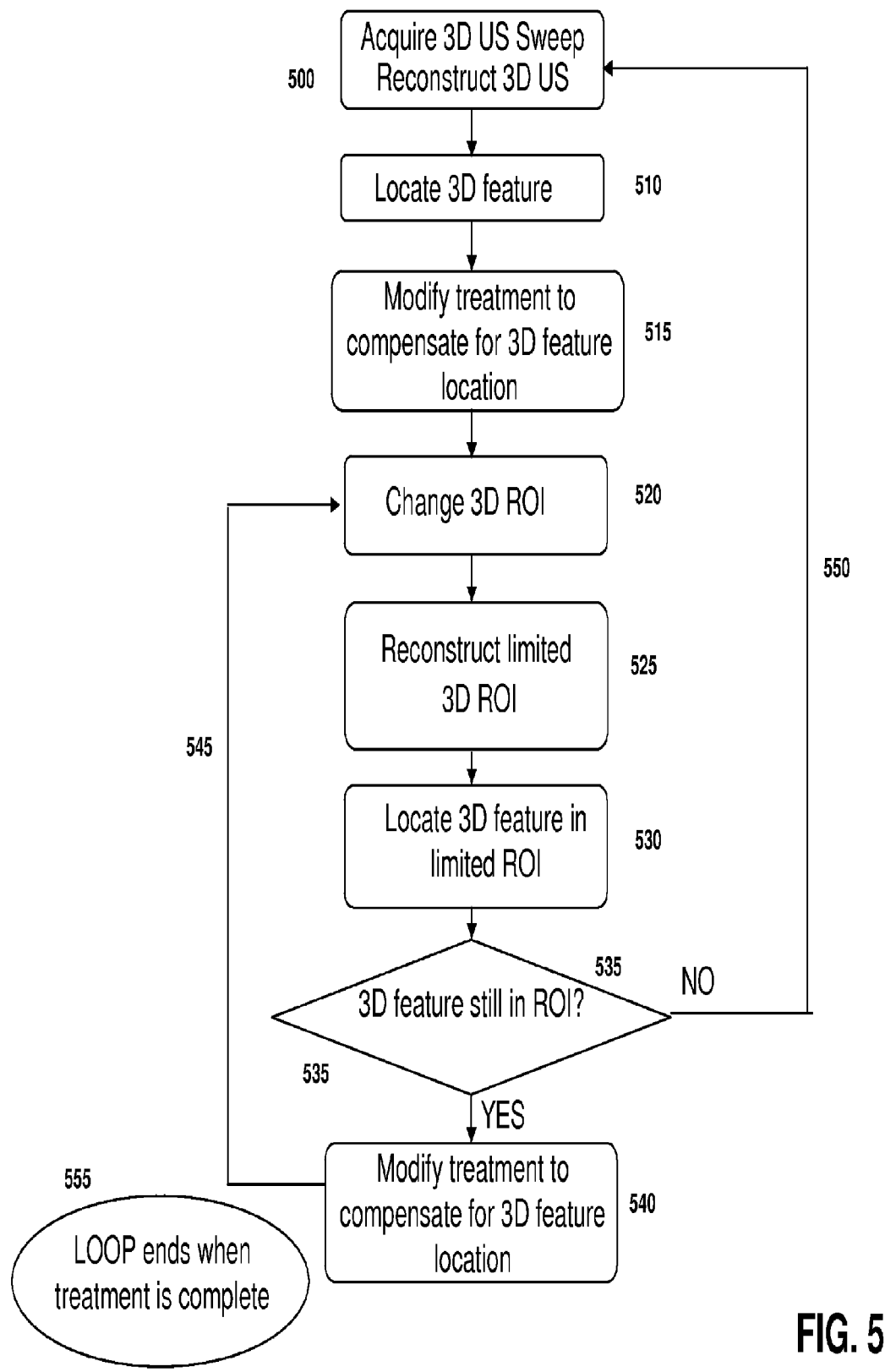
FIG. 5 is a flow-chart illustrating a particular implementation of a hybrid three-dimensional and limited ROI three-dimensional temporal tracking strategy according to various embodiments of the invention.
Figure 6:
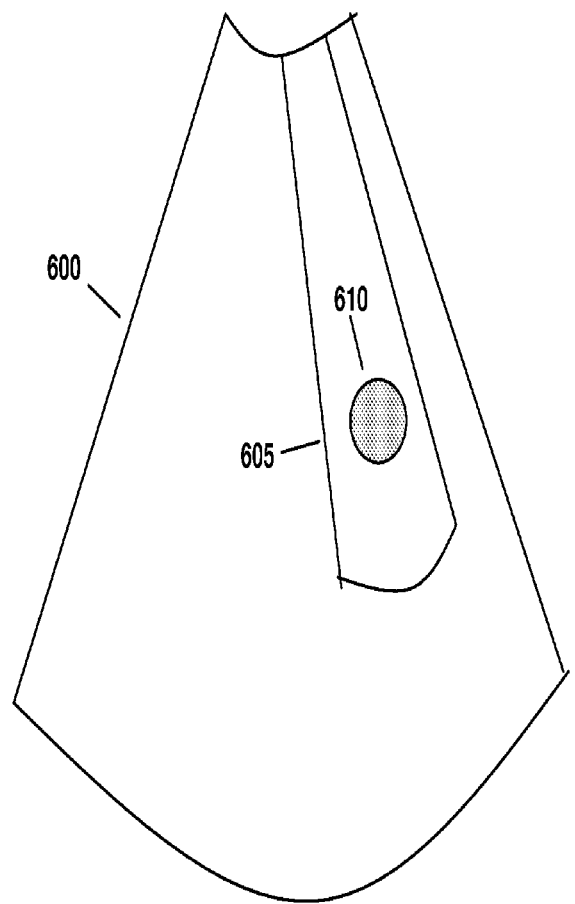
FIG. 6 illustrates a particular implementation of a hybrid three-dimensional and multiple two-dimensional plane temporal tracking in which the image extent encompassing the feature being treated is reduced according to various embodiments of the invention.

FIG. 5 illustrates an alternative approach. Steps 500-515 are the same as steps 200-215 of FIG. 2, respectively. In step 520, the region of interest (ROI) of the three-dimensional volume is reduced such that it encompasses only the feature plus a limited amount of surrounding voxels. This is accomplished by limiting the sector size of the two-dimensional ultrasound frames throughout the sweep and/or the extent of the sweep, in some cases asymmetrically, as well as the depth of penetration. Referring to FIG. 6 as an example, the full sector size and depth, leading to image extent 600, are reduced to form the image extent 605 which encompasses the feature 610 with a small amount of padding. Reducing sector size and/or depth increases the frame-rate, which allows for faster sweeping motion while still acquiring sufficient slices for high resolution three-dimensional image reconstruction. In other examples, the number of imaging lines per frame ("line density") is decreased which increases the frame rate, but at the expense of resolution. The range of X values for the sweeping motion can also be limited, which increases the three-dimensional image acquisition as well. Many more temporal three-dimensional images can be acquired, but due to the smaller region, the risk that the feature moves outside of the limited ROI increases.

Returning to FIG. 5, the limited three-dimensional ROI is reconstructed (step 525), and due to the smaller number of voxels, the speed of the reconstruction process is increased and the memory requirements are reduced as compared to a full three-dimensional reconstruction. In step 530, the location of the three-dimensional feature within the limited ROI is determined. In step 535, if the feature has remained in the limited ROI, step 545 is executed, continuing the tracking of the feature within the limited ROI. The ROI can be re-modified in step 520 to account for any new positioning of the feature. If the feature is no longer within the limited ROI, or getting too close to a boundary, then step 550 allows for a full ROI reconstruction prior to limiting the ROI again for further tracking. In some cases, full ROI sweeps are also acquired at various time intervals. The loop ends when treatment is complete, as represented by step 555.

Strategy 5: Hybrid Three-dimensional and Multiple Two-dimensional Plane Temporal Tracking with Reduced Sector Size In another approach, two tracking planes are used—the first plane is a pure two-dimensional ultrasound at a fixed X position of the motorized probe as described above (the X position can be adjusted to include the tracked feature as its position is updated), and the second plane is a reconstructed plane which is orthogonal or near-orthogonal to the first plane. The ultrasound data in the second plane is acquired with a very small sector size, ideally approaching zero, so that the sweep can be performed quickly. In some variations, the sector size is very small during most of the sweep, is rapidly increased as the sweep crosses through X of the pure ultrasound plane, then reduced quickly again to complete the acquisition of reconstructed plane.

Locating an anatomical feature according to one or more of the methods described above can be performed by drawing a structure (i.e., either manually, semi-automatically, or automatically) corresponding to an anatomical feature illustrated in a first image. This first image can, for example, be an image from a previous planning session, a previous treatment session, or an image obtained for a first interfractional motion correction prior to tracking In most applications of interest, the structure being tracked does not change shape while the patient is on the table. Thus, the original structure can be moved from image to image, keeping its shape intact, so that it best-fits each image. The amount the structure is moved within an image provides a distance the anatomical feature has travelled between each successive image. If image acquisition is fast enough, motion between successive images is small and easier to track. This applies to both two-dimensional contours in planes as well as three-dimensional contours.

In some cases, the techniques described above may be combined with another method of intrafractional motion detection. For example, the literature describes tracking fiducials with the treatment beam. This method, although requiring invasive fiducials, has the benefit of not introducing additional imaging radiation since the treatment beam itself is used for tracking. However, using this approach the detection of prostate motion is limited to the plane perpendicular to the beam, and therefore motion in other directions must be modeled with assumptions. Furthermore, changing beam apertures can obscure the fiducials, leading to times when prostate motion is unknown.

In a particular embodiment used to track and compensate for prostate motion during a radiotherapy treatment, the patient is first imaged with a full 3D sweep. The prostate, and in some cases other critical structures, are localized with or without user assistance from this first image. Rapid sweeps are then effectuated through a central part of the prostate, typically the central ⅔ of the prostate. This decreases the sweep time, but also ensures the 2D images acquired during the sweep are focused on the prostate and therefore give useful information to detect its motion. To decrease sweep time even further, factor such as line density, sector size and depth are optimized to increase frame rate and thus the amount of time it takes to acquire a sweep. The direction of sweep may be alternated (e.g., left-to right, then right-to-left) to minimize delay between sweeps. The resolution of the sweep is determined partially by the angular distance between successive 2D acquisitions, and is also optimized to increase speed while maintaining a clinically relevant resolution. By modifying these parameters, a frame rate of 50 Hz or more can be achieved. For transperineal imaging of the prostate with a mechanically sweeping probe, a sweep angle of 30 degrees is preferred, with an acceptable range being between 15 and 60 degrees. Assuming an angular resolution of 0.5 degrees, a sweep time on the order of one second may be achieved.

The positioning of the acquired 2D frames should be accurately positioned in space based on the room coordinates. Although this accuracy is governed by the calibration process, the process should reproducible under real situations, for example in instances in which the motor that moves the probe slips. For this reason, a secondary mechanism may be included to verify the stability of the probe as it is sweeping. For example, a Hall sensor or optical sensor can be used to detect when the probe sweeps past a central position. The consistency of the sweeping through the central position can be verified to validate a sweep, or in some cases, used to correct for an offset.

If the sweep time of the probe is too long, each 2D image is no longer in strict geometric plane in room coordinates, but instead a curved surface. In some embodiments, the spatial positioning of the pixels from a 2D image are warped to account for this bending of image planes.

As the 2D images are acquired during a sweep, they are successively stored in a register to form an image. As the probe continues to sweep, the image data aquired at each postion overwrites the image data acquired from the last time the probe was at that position. Thus, at least certain portions of the set of targeted 2D images in the register are constantly being updated.

In certain embodiments, a registration algorithm is used to detect changes in the partially updated image over time. If, for example, the algorithm takes 0.5 seconds to execute, a displacement will be known every 0.5 seconds. The sampling interval is thus a result of the algorithm calculation time rather than the sweep time. The displacement, however, is calculated from a partially updated image and is thus not a completely new displacement measurement.

For prostate treatments, it may, in some instances, be sufficient to assume the prostate exhibits translations and rotations only, and that deformations are negligible. Thus a rigid intensity-based registration algorithm can be used to calculate prostate displacements in a given image relative to a reference image. In one particular case, a trust-region gradient descent optimizer with a normalized cross-correlation as a cost function may be used. A mask may be placed around the prostate to reduce the algorithm computation time.

If an angular mechanically sweeping probe is used, the acquired collection of 2D images are not perpendicular to one another but can naturally be described using a cylindrical coordinate system. Typical registration algorithms, however, require voxel data in a Cartesian coordinate system. Although the data could be reconstructed into a Cartesian coordinate system such as with the full 3D sweep data, this would significantly increase the calculation time which is to be minimized for targeted subset sweeps. Therefore, registration may be performed directly using cylindrical coordinates when an angular sweeping probe is used, as described below. Registration may also be performed using a multiscale approach, in which the images are first reduced in size and then sequentially registered at successively more detailed scales, in order to decrease calculation time. Each time a registration is calculated, the quality factor of the registration (quantified by the normalized cross-correlation in this case) is evaluated and, in some cases, checked against a threshold.

Registration can quantify not only prostate motion, but also changes in surrounding critical structures. Although the prostate itself can be considered to undergo rigid transformations to good approximation, critical structures such as the penile bulb can follow an independent motion, and therefore tracking of critical structures is not well suited for non-rigid transformations that include deformations. For example, a B-Spline transformation may be used together with a Broyden-Fletcher-Goldfarb-Shanno (BFGS) optimizer. The BFGS optimizer can converge more robustly and quickly in higher dimensional parameter spaces without requiring the calculation of the Hessian matrix of the cost function. The gradient descent optimizer would tend to be slow, and to stop prematurely, before reaching an optimal value.

In practice, if the time taken to perform a registration is designated as $\Delta t_R$, and the time to acquire a full sweep is designated as $\Delta t_s$, six degrees of freedom of prostate motion are calculated once every $\Delta t_R$ throughout the radiation treatment on the partially updated image stored in the register. In addition, a quality factor Q (assuming deformations are ignored) may also be determined. Limits are set on the six degrees of motion and Q such that they can only be out of tolerance for a predetermined length of time T. Limits can also be set on displacements of critical structures. If this occurs, the beam is stopped, and a full 3D sweep is initiated to calculate an adjustment to the six degrees of freedom (the adjustments can be limited to translations only for practical reasons). These adjustments are used to modify the position and orientation of the treatment couch in order to re-align the prostate prior to resuming treatment. In some cases, as previously described, the couch adjustments are carried out at regular intervals throughout treatment.

Incorporation of the quality factor Q allows the treatment to be temporarily interrupted if the prostate tracking is or becomes unreliable. Furthermore, if the prostate moves rapidly and significantly during the length of a sweeps $\Delta t_s$, this will show up as a deformation or discontinuity in the partially updated image, which will affect the quality factor Q. Such motions can be acceptable in the occasional sweep, but the treatment is ideally interrupted if the prostate moves rapidly over many sweeps.

Since the patient couch moves during treatment, and the probe is affixed to the couch, the cylindrical coordinate system is not constant in the room coordinate system. Ideally, this is taken into account by knowledge of the couch-to-room transformation, which can be known by tracking the couch at all times.

In the preferred embodiment, a display tracks changes in prostate displacements on a screen with visual or aural when it is out of tolerance. The registration transformations are displayed as updated segmentations on the screen in orthogonal views such as axial, sagittal and coronal.

In some cases, the targeted 2D images acquired at a given sweep position are registered to a 2D reference plane from the same sweep position acquired at a previous time. 2D registration algorithms are generally faster than 3D algorithms. These 2D registrations allow an a calculation of target motion which is approximate but fast, thus allowing to estimate when the prostate has moved within a sweep. This helps to determine whether a sweep is representative of a relatively stable prostate position or if it is based on rapid prostate motion and thus unreliable for registration purposes, contributing to the quality factor Q. This strategy also complements the preferred embodiment by providing more finely sampled, albeit approximate, displacements.

Although the specific applications above utilize a mechanized three-dimensional probe, other types of three-dimensional probes can be used as well. For example, matrix probes, which consist of a two-dimensional surface of piezoelectric elements, can acquire full three-dimensional ultrasound datasets. Bi-planar probes, which can simultaneously acquire two perpendicular slices of two-dimensional ultrasound data, can also be used in some embodiments.

Figure 7:
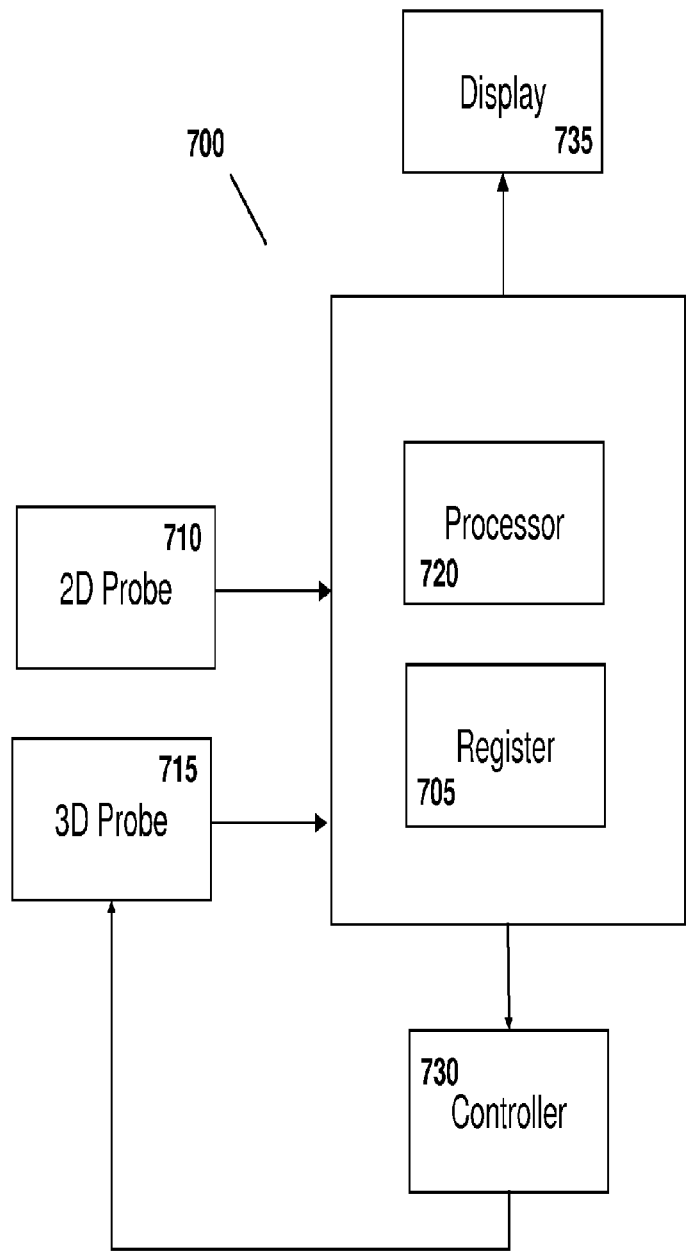
FIG. 7 illustrates a system for tracking intrafractional motion during the course of radiotherapy according to various embodiments of the invention.

Referring to FIG. 7, a system 700 for performing the techniques described above includes a register 705 or other volatile or non-volatile storage device that receives image data from the ultrasound imaging probe(s) 710 and/or 715 via a cord or wire, or in some embodiments via wireless communications. The system also includes a processor 720 that, based on the image data, uses the techniques described above to create three-dimensional, time-based images of the region of interest and determine if the feature being treated has moved and/or morphed such that the displacement or changes in shape or size require adjustments to image parameters used to capture subsequent images. The processor calculates any necessary adjustments and, in some cases, provides updated imaging parameters to a controller 730. The controller 730 directs the probe(s) 710 and/or 715 to implement the adjustments either mechanically (e.g., by changing the physical location of the probe within its housing or implementing positional adjustments directly or using a brace, arm or other support device) or electronically (e.g., by altering the power delivered to the probes and/or frequency of the ultrasound energy). As such, the feature remains in the region being imaged throughout the entire imaging and treatment process.

In some embodiments, a display 735 and an associated user interface may also be included, thus allowing a user to view and manipulate the images and/or treatment parameters. The display 735 and user interface can be provided as one integral unit (as shown) or separate units and may also include one or more user input devices such as a keyboard and/or mouse. The display can be passive (e.g., a "dumb" CRT or LCD screen) or in some cases interactive, facilitating direct user interaction with the images and models through touch-screens (using, for example, the physician's finger as an input device) and/or various other input devices such as a stylus, light pen, or pointer. The display 735 and input devices may be in location different from that of the register 705 and/or processor 720, thus allowing users to receive, view, and manipulate images in remote locations using, for example, wireless devices, handheld personal data assistants, notebook computers, among others.

In various embodiments the register and/or processor may be provided as either software, hardware, or some combination thereof. For example, the system may be implemented on one or more server-class computers, such as a PC having a CPU board containing one or more processors such as the Pentium or Celeron family of processors manufactured by Intel Corporation of Santa Clara, Calif., the 680x0 and POWER PC family of processors manufactured by Motorola Corporation of Schaumburg, Ill., and/or the ATHLON line of processors manufactured by Advanced Micro Devices, Inc., of Sunnyvale, Calif. The processor may also include a main memory unit for storing programs and/or data relating to the methods described above. The memory may include random access memory (RAM), read only memory (ROM), and/or FLASH memory residing on commonly available hardware such as one or more application specific integrated circuits (ASIC), field programmable gate arrays (FPGA), electrically erasable programmable read-only memories (EEPROM), programmable read-only memories (PROM), programmable logic devices (PLD), or read-only memory devices (ROM). In some embodiments, the programs may be provided using external RAM and/or ROM such as optical disks, magnetic disks, as well as other commonly storage devices.

For embodiments in which the invention is provided as a software program, the program may be written in any one of a number of high level languages such as FORTRAN, PASCAL, JAVA, C, C++, C#, LISP, PERL, BASIC or any suitable programming language. Additionally, the software can be implemented in an assembly language and/or machine language directed to the microprocessor resident on a target device.

It will therefore be seen that the foregoing represents an improved method and supporting system for tracking features over the course of a medical procedure. The terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed. Moreover, although the above-listed text and drawings contain titles headings, it is to be understood that these title and headings do not, and are not intended to limit the present invention, but rather, they serve merely as titles and headings of convenience.

What is claimed is:

1. A computer-implemented method utilizing a processor executing computer-executable instructions for tracking an anatomical feature of interest using an imaging device, the method comprising:
   receiving a series of three dimensional images of a region of interest acquired by the imaging device at a first image acquisition rate, wherein the region of interest includes the anatomical feature of interest;
   determining, by the processor, a location of the anatomical feature of interest in the region of interest;
   receiving temporally-displaced targeted subsets of ultrasound images acquired by the imaging device at a second image acquisition rate greater than the first image acquisition rate for the determined location;
   comparing, by the processor, each targeted subset with at least one of the three dimensional images;
   determining, by the processor, a displacement of the anatomical feature based on each comparison; and
   using the determined displacement to determine whether to modify a radiation therapy treatment plan.

2. The computer-implemented method of claim 1, further comprising:
   determining if the displacement of the anatomical feature exceeds a displacement threshold; and
   obtaining an updated three dimensional image of the region of interest according to the first image acquisition rate prior to a scheduled update.

3. The computer-implemented method of claim 2, wherein the displacement threshold comprises an upper limit of the anatomical feature of interest.

4. The computer-implemented method of claim 1, further comprising:
   determining if the displacement exceeds a safety threshold; and
   causing a medical procedure to stop to allow for an adjustment.

5. The computer-implemented method of claim 1, further comprising adjusting one or more image parameters used in obtaining the targeted subsets of images based on the displacement.

6. The computer-implemented method of claim 1, further comprising adjusting at least one of a treatment couch, a multi-leaf collimator, or a combination thereof in response to the displacement during treatment of the anatomical feature.

7. The computer-implemented method of claim 1, wherein the targeted subset comprises a plurality of two dimensional image slices of the anatomical feature.

8. The computer-implemented method of claim 1, wherein the targeted subset comprises two or more tracking planes having two-dimensional images of the region of interest.

9. The computer-implemented method of claim 8, wherein one or more of the tracking planes comprise at least one reconstructed plane including a voxel set attached to a single plane that passes through the region of interest.

10. The computer-implemented method of claim 8, wherein the one or more tracking planes comprise a first tracking plane that is orthogonal to a second tracking plane, wherein the first tracking plane and the second tracking plane include two-dimensional images of the region of interest.

11. The computer-implemented method of claim 1, wherein the targeted subset further comprises a plurality of three dimensional datasets related to a limited region of interest.

12. The computer-implemented method of claim 11, wherein the limited region of interest is based at least in part on an adjusted sector size parameter.

13. The computer-implemented method of claim 11, wherein the limited region of interest is based at least in part on an adjusted image depth parameter.

14. The computer-implemented method of claim 11, wherein the limited region of interest is based at least in part on an adjusted ultrasound sector angle.

15. The computer-implemented method of claim 1, wherein obtaining the targeted subsets at the second image acquisition rate greater than the first image acquisition rate, further comprises obtaining three dimensional datasets having a reduced image resolution.

16. The computer-implemented method of claim 1, further comprising obtaining the three dimensional images using at least one of a motorized probe, a biplanar probe, and a matrix probe associated with the imaging device.

17. The computer-implemented method of claim 1, wherein a fiducial is embedded in the anatomical feature, and wherein comparing each subset with at least one of the three dimensional images further comprises comparing images of the fiducial in the subset and the at least one of the three dimensional images.

18. The computer-implemented method of claim 1, wherein the anatomical features of a patient comprises at least one of a target lesion, one or more subsets of the target lesion, or a fiducial.

19. The computer-implemented method of claim 1, wherein modifying the radiation therapy treatment plan is based on a registration algorithm using the displacement to determine changes in the anatomical feature.

20. The computer-implemented method of claim 19, wherein the displacement is determined from a partially updated image.

21. The computer-implemented method of claim 1, wherein the radiation therapy treatment plan is modified in real-time.

22. The computer-implemented method of claim 1, wherein the displacement is a positional displacement determined in real-time.

* * * * *

UNITED STATES PATENT AND TRADEMARK OFFICE
CERTIFICATE OF CORRECTION

| | |
|---|---|
| PATENT NO. | : 9,248,316 B2 |
| APPLICATION NO. | : 13/239795 |
| DATED | : February 2, 2016 |
| INVENTOR(S) | : Martin Lachaine et al. |

It is certified that error appears in the above-identified patent and that said Letters Patent is hereby corrected as shown below:

In the claims,

Claim 7, col. 16, line 63, "the targeted subset" should read --each targeted subset--.

Claim 8, col. 16, line 66, "the targeted subset comprises two or more" should read --each targeted subset comprises one or more--.

Signed and Sealed this
Twelfth Day of April, 2016

Michelle K. Lee
*Director of the United States Patent and Trademark Office*